US00PP26993P3

(12) United States Plant Patent
Wood

(10) Patent No.: US PP26,993 P3
(45) Date of Patent: Aug. 2, 2016

(54) ***SPIRAEA* PLANT NAMED 'SMNSJMFR'**

(50) Latin Name: *Spiraea japonica*
Varietal Denomination: SMNSJMFR

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 17 days.

(21) Appl. No.: 14/544,337

(22) Filed: Dec. 23, 2014

(65) Prior Publication Data

US 2016/0183426 P1 Jun. 23, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/0216; A01H 5/02
See application file for complete search history.

*Primary Examiner* — Kent L Bell
(74) *Attorney, Agent, or Firm* — Cassandra Bright

(57) ABSTRACT

A new and distinct *Spiraea* cultivar named 'SMNSJMFR' is disclosed, characterized by a extremely abundant flowering, attractive dark burgundy red foliage in the Spring, and red flowers. The new variety is a *Spiraea*, normally produced as an outdoor garden or container plant.

3 Drawing Sheets

Latin name of the genus and species: *Spiraea japonica*.
Variety denomination: 'SMNSJMFR'.

BACKGROUND OF THE INVENTION

The new *Spiraea* cultivar is a product of a planned breeding program conducted by the inventor, Timothy D. Wood, in Grand Haven, Mich. The objective of the breeding program was to produce new *Spiraea* varieties of compact, full plant habit with novel and improved flower and leaf colors. The open pollination resulting in this new variety was made during June of 2007.

The parents are unknown varieties of *Spiraea japonica*; seed was bulk collected and actual parents not identified. In a block of 100 mature, flowering, unnamed seedlings that had been pretreated with 10 greys of radiation, seed was collected from ten plants evaluated to have the best foliage and flowers. This collected seed was grown out and seedlings selected for superior foliage, flower coverage and flower color. The new variety was identified as a potentially interesting selection in June of 2009, at a greenhouse in Grand Haven, Mich.

Asexual reproduction of the new cultivar 'SMNSJMFR' by softwood cuttings was first performed during June of 2009, at commercial greenhouse in Grand Haven, Mich. Subsequent propagation has shown that the unique features of this cultivar are stable and reproduced true to type in 3 successive generations.

SUMMARY OF THE INVENTION

The cultivar 'SMNSJMFR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNSJMFR'

These characteristics in combination distinguish 'SMNSJMFR' as a new and distinct *Spiraea* cultivar:

1. True red flowers whereas *Spiraea* typically have pink flowers.
2. Attractive dark burgundy red foliage in the Spring.
3. Extremely abundant flowering.

PARENT COMPARISON

Parents are unknown.

COMMERCIAL COMPARISON

Plants of the new cultivar 'SMNSJMFR' can be compared to the commercial variety *Spiraea* 'Galen', U.S. Plant Pat. No. 21,712. These varieties are similar in most horticultural characteristics; however 'SMNSJMFR' differs in the following:

1. Red flowers. The comparator's flowers are purplish-pink.
2. Darker red Spring foliage.
3. More abundant flowering.

Plants of the new cultivar 'SMNSJMFR' can also be compared to the unpatented commercial variety *Spiraea* 'Dart's Red'. These varieties are similar in most horticultural characteristics; however 'SMNSJMFR' differs in the following:

1. Red flowers. The comparator's flowers are dark pink.
2. Dark red foliage in the Spring. The comparator's Spring foliage is green.

BRIEF DESCRIPTION OF THE PHOTOGRAPHS

The accompanying photograph in FIG. 1 illustrates in full color a typical plant of 'SMNSJMFR' grown in an outdoors in Grand Haven, Mich.

Figure 1:
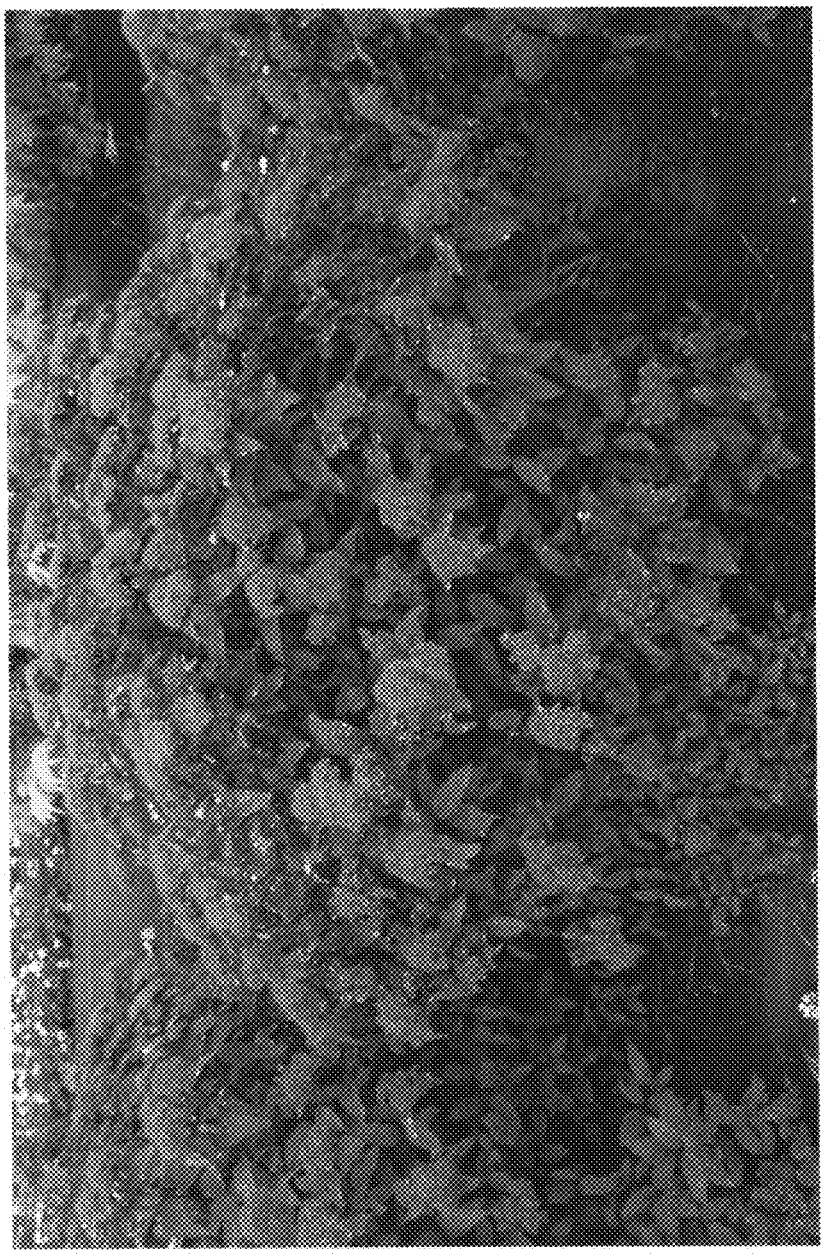
Figure 2:
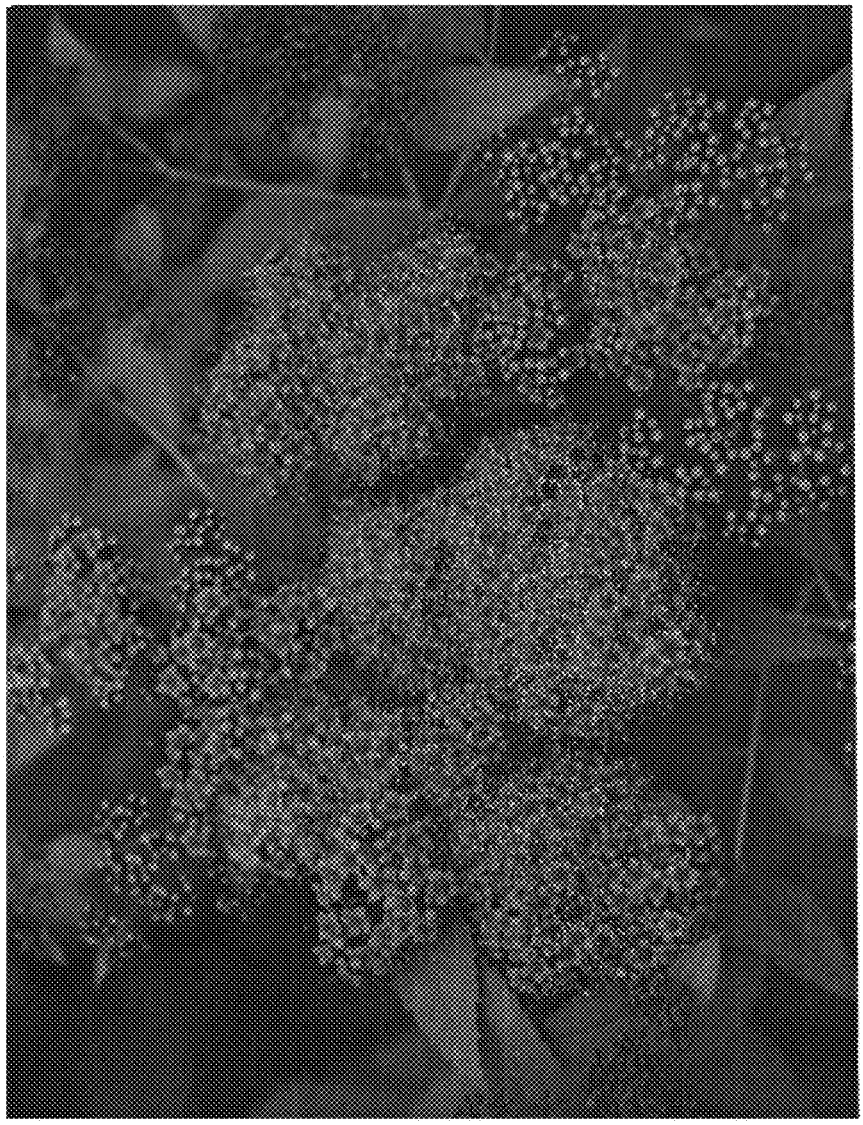
FIG. 2 illustrates in full color a typical flower of 'SMNSJMFR'.
Figure 3:
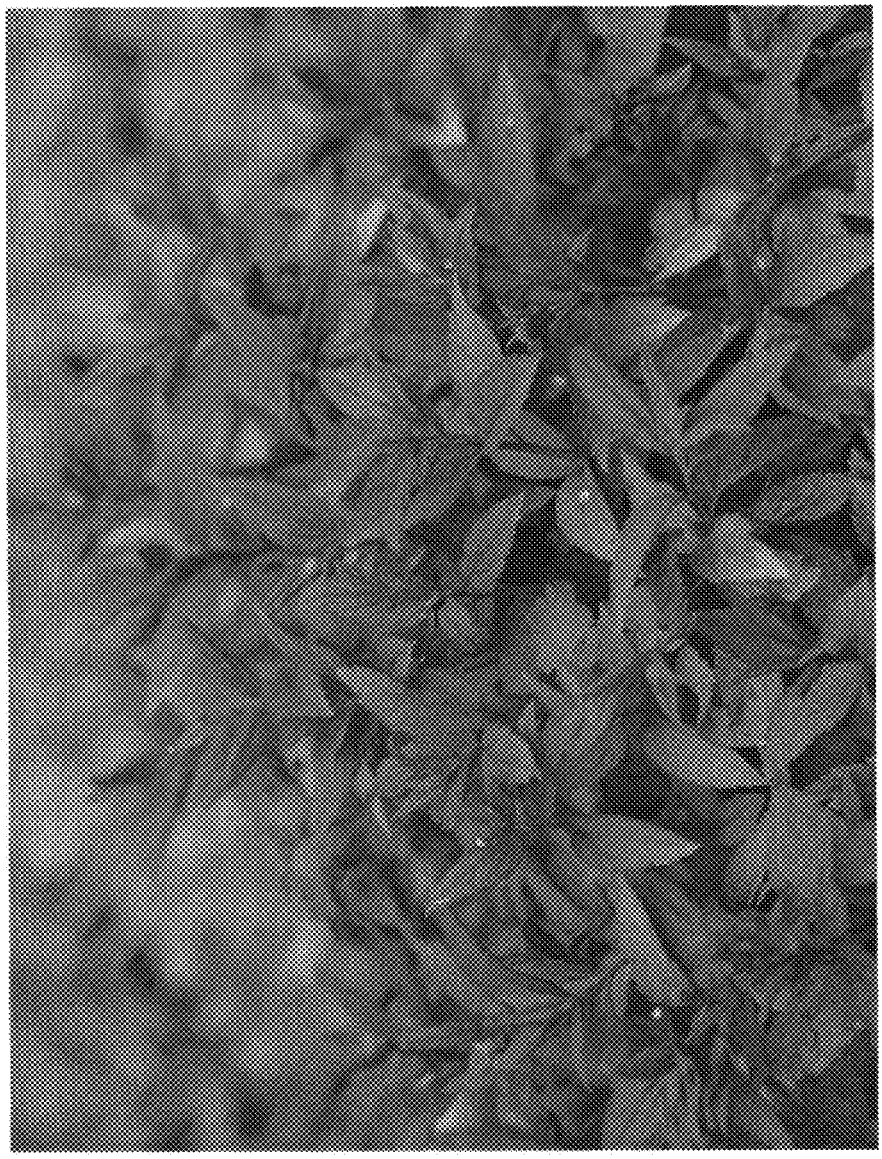
FIG. 3 illustrates in full color the burgundy red Spring foliage.

Age of the plant photographed is approximately 2 years. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'SMNSJMFR' plants grown in a commercial nursery in Grand Haven, Mich. Measurements were taken during Summer. The plants were 2 years old and in 3 gallon containers. The growing temperature ranged from 10° C. to 38° C. The greenhouse is double poly covered though the winter. Measurements and numerical values represent averages of typical plant types.

Botanical classification: *Spiraea japonica* 'SMNSJMFR'.

PROPAGATION

Time to initiate roots: About 15 days at approximately 22° C.

Root description: Fibrous, moderate to dense density medium thickness and freely branching. Cream to brown in color, not effectively measured with a color chart.

Time to produce a rooted young plant: About 2 months at 22° C.

PLANT

Plant type: Perennial shrub.

Age of plant described: Approximately 2 years old.

Growth habit: Rounded habit with good, strong branching.

Pot size of plant described: 3 gallon pot.

Overall plant shape: Upright and rounded.

Height: Approximately 30 cm to top of foliage.

Plant spread: Approximately 57 cm.

Growth rate: Fast.

Plant vigor: Strong.

Branching characteristics: Good, commonly branches at terminal internodes. Some basal branching, some pinching required.

Length of primary lateral branches: Approximately 33 cm.

Diameter of lateral branches: Approximately 2.5 mm.

Quantity of lateral branches: Average 15.

Stem:

- *Stem appearance*.—Rounded, glabrous.
- *Stem strength*.—Strong after 1 year of age.
- *Stem color*.—New growth: Near RHS Yellow-Green 144B. Bark: Near RHS Greyed-Orange 165A.
- *Pubescence*.—None.
- *Aspect*.—Straight, growing at an outward angle of 45°.
- *Other plant characteristics*.—Strong red Fall leaf color and orange/red Spring growth.

Internode length: Average 1 cm.

FOLIAGE

Leaf:

- *Arrangement*.—Alternate, single.
- *Leaf shape*.—Ovate.
- *Quantity*.—Approximately 12 fully expanded per main branch.
- *Average length*.—Approximately 4.5-5.5 cm.
- *Average width*.—Approximately 1.5-2 cm.
- *Apex*.—Acute.
- *Base*.—Cuneate.
- *Margin*.—Double serrate.
- *Texture of top surface*.—Smooth, glabrous.
- *Texture of bottom surface*.—Smooth, interrupted by protruding leaf veins.
- *Color*.—Young foliage upper side: Outer edge: Near RHS Red-purple 59A. Base of leaf: Near RHS Yellow-green 144A. Young foliage under side: Outer edge: Near RHS Red-purple 59A. Base of leaf: Near RHS Yellow-green 144A. Mature foliage upper side: Near RHS Green 141A. Mature foliage under side: Near RHS Green 139B.
- *Venation*.—Pattern: Palmate. Color upper side: Near RHS Yellow-green 145C. Color under side: Near RHS Yellow-green 145C.
- *Petiole*.—Average Length: Approximately 3 mm. Diameter: 1 mm. Petiole color upper side: Near RHS Yellow-Green 145C. Petiole color lower side: Near RHS Yellow-Green 145C. Petiole Texture upper side: Smooth, cupped. Petiole Texture lower side: Smooth, rounded. Stipules characteristics: Stipules at every internodes, 2 mm long, near RHS Yellow-green 145B.

FLOWER

Natural flowering season: Late Spring through the Summer.

Flower arrangement: Single whorled rotate flowers.

Inflorescence type and habit: Terminal corymb.

Quantity of flowers per inflorescence: Over 100.

Inflorescence size:

- *Width*.—Approximately 5 cm.
- *Height*.—Approximately 3.5 cm.

Quantity of flowers per lateral stem: Several hundred.

Quantity of flower buds per lateral stem: Average 2000 to 3000.

Quantity of flowers per plant: Average 5000 to 8000.

Individual flowers:

- *Flower form*.—Rotate.
- *Flower aspect*.—Upright and outward.
- *Size*.—Diameter: Approximately 8 mm. Depth: Approximately 5 mm.
- *Flower other characteristics*.—Persistence: Self cleaning. Fragrance: Slight, sweet.

Petal:

- *Petal arrangement*.—Single whorl of five petals.
- *Number of petals per flower*.—5.
- *Petal shape*.—Globular.
- *Petal base*.—Obtuse.
- *Margin*.—Entire.
- *Tip shape*.—Obtuse.
- *Length*.—2 mm.
- *Width*.—3 mm.
- *Texture*.—Upper: Smooth, Glabrous. Lower: Smooth, Glabrous.

Petal color:

- *When opening*.—Upper surface: Near RHS Red-purple 70A. Lower surface: Near RHS Purple-violet 81B.
- *Fully opened*.—Upper surface: Near RHS Red-purple 70B. Lower surface: Near RHS Red-purple 74C.

*Fading to*.—Upper surface: Near RHS Purple-violet 81C. Lower surface: Near RHS Purple-violet 81C.

Bud:

*Shape*.—Globose.

*Length*.—Approximately 2 mm.

*Diameter*.—Approximately 2 mm.

*Color*.—Base of bud: Near RHS Yellow-green 147A. At tip: near RHS Red-purple 59C.

Sepals:

*Shape*.—Acute.

*Arrangement*.—Single whorl of 5 sepals.

*Number of sepal*.—5.

*Length*.—Approximately 1 mm.

*Width*.—Approximately 1 mm.

*Margin*.—Entire.

*Base*.—Fused.

*Tip*.—Acute.

*Texture*.—Smooth, glabrous.

*Mature color*.—Upper side: Near RHS Red-purple 59A. Lower side: Near RHS Green 131A.

Peduncle:

*Length*.—4.2 mm.

*Diameter*.—5 mm.

*Color*.—Near RHS Yellow-green 144A.

*Orientation*.—Upright and outward.

*Strength*.—Strong.

*Texture*.—Smooth, glabrous.

Pedicel:

*Length*.—6 mm.

*Diameter*.—0.5 mm.

*Color*.—Near RHS Yellow-green 144B.

*Orientation*.—Upright and outward.

*Strength*.—Strong.

*Texture*.—Smooth.

REPRODUCTIVE ORGANS

Stamens:

*Number*.—Over 20.

*Filament length*.—4 mm.

*Filament color*.—Near RHS Purple 78C.

Anthers:

*Shape*.—Globose.

*Length*.—Approximately 0.25 mm.

*Color*.—Near RHS Black 202A.

*Pollen color*.—RHS White 155D.

*Amount of pollen*.—Very little.

Pistil:

*Number*.—5.

*Length*.—Approximately 2 mm.

*Style*.—Length: Approximately 0.5 mm. Color: Near RHS Red-purple 71C.

*Stigma*.—Shape: Globose. Color: Near RHS Red-purple 71C. Ovary color: Near RHS Yellow-green 144C.

OTHER CHARACTERISTICS

Seeds and fruits: Not observed to date.

Garden performance: Excellent performance in a garden setting.

Disease/pest resistance: Good mildew resistance observed. Neither resistance nor susceptibility to normal diseases and pests of *Spiraea* have been observed.

Temperature tolerance: The new variety tolerates temperatures between −31° C. to 38° C.

What is claimed is:

1. A new and distinct cultivar of *Spiraea* plant named 'SMNSJMFR' as herein illustrated and described.

* * * * *